United States Patent [19]

McGredy

[11] Patent Number: Plant 6,907

[45] Date of Patent: Jul. 11, 1989

[54] ROSE PLANT

[76] Inventor: Samuel McGredy, 130 B Beach Road, Castor Bay, Auckland 9, New Zealand

[21] Appl. No.: 83,040

[22] Filed: Aug. 7, 1987

[51] Int. Cl.[4] ..... A01H 5/00

[52] U.S. Cl. ..... Plt./7

[58] Field of Search ..... Plt. 7, 10

*Primary Examiner*—Robert E. Bagwill

[57] ABSTRACT

A new miniature rose variety of variegated red and white flower coloring.

1 Drawing Sheet

The present invention relates to a new and distinct variety of rose plant of the miniature rose class, which was originated by crossing as seed parent the rose known as "Eyepaint" and as pollen parent the rose known as "Ko's Yellow". The varietal denomination of this new variety is "Macmanly".

Among the novel characteristics possessed by this new variety which distinguish it from its parents and all other varieties of which I am aware are its variegated red and white petals which change to a brilliant solid red with a white eye or center as the bloom matures. Flowers are long lasting on the plant and after cutting. Asexual reproduction by budding and cuttings of the new variety as performed in Washington County, Ore., shows that the foregoing and other distinguishing characteristics come true to form and are established and transmitted through succeeding propagations.

The accompanying picture shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "137B" is plate 137B of The Royal Horticultural Society Colour Chart.

Parentage: Seedling.
*Seed parent.*—"Eyepaint".
*Pollen parent.*—"Ko's Yellow".
Class: Miniature.

The following observations are made of specimens grown out doors in Washington County, Ore., during July.

FLOWER

Blooming habit: Near continuous.

A. Bud:
(1) *Size.*—Small, about 1½ cm.
(2) *Form.*—Pointed.
(3) *Color.*—When sepals first divide you see the reverse of the petals — a solid cream color.
(4) *Sepals.*—Spear shaped, reflexed, ⅓ cm. longer than bud.
(5) *Peduncle.*—Length — about 2½ cm. Aspect — straight. Strength — erect. Color — near 137C.

B. Bloom:

(1) *Size.*—Average size when fully expanded — about 3 cm.
(2) *Borne.*—Several to a stem.
(3) *Form.*—Informal, decorative, smooth petals Opening outward becoming a semi-double bloom.
(4) *Petalage.*—Number of petals under normal conditions — About 12 to 16.
(5) *Color.*—After sepals fall, visible bud coloring is cream on reverse of petals and showing yellow base 16B. The inner petals are faintly striped or variegated with shades of red 46D and 46C. The inner petal base is yellow 20B involving ⅓ of the petal surface. Bloom opens flat showing yellow center and stamens. As the bloom ages the yellow base center matures to white and the variegated red coloring turns to bright solid red 46B.

C. Petals:
(1) *Texture.*—Moderately thick and of good substance.
(2) *Appearance.*—Inside — velvety, outside velvety.
(3) *Form.*—Outer petals are pointed with smooth edge, inner petals also pointed
(4) *Arrangement:*—Regularly arranged
(5) *Petaloids in center.*—Medium.
(6) *Persistence.*—Drop off cleanly.
(7) *Fragrance.*—Moderate.
(8) *Lasting quality.*—Very long lasting on plant and blooms last 7 days as cut flower.

REPRODUCTIVE ORGANS

A. Stamens, filaments and anthers:
(1) *Arrangement.*—Regularly arranged stamens around high pistils.
(2) *Color.*—Medium yellow.

B. Pollen:
*Color.*—Light Yellow.

C. Styles: Even length — introse.

D. Stigmas:
*Color.*—Light yellow.

E. Hips: Globular, usually formed, about ¾ cm, orange, seeds do not protrude.

F. Sepals: Permanent, spear shaped, reflexed.

PLANT

A. Form: Rounded, dwarf, bushy.

B. Growth: Uniform branching, medium vigor.
*Height attained.*—About 32 cm.

C. Foliage: Compound 5 leaflets.
(1) *Size.*—Medium 1 cm leaflets.

(2) *Quantity.*—Abundant.

(3) *Color.*—New foliage: Upper side — near to 137B. Under side — near to 138B. Old foliage: Upper side — near 137B. Under side — near 138B.

(4) *Shape.*—Oval pointed, supported by petiolule.

(5) *Texture.*—Upper side is glossy.

(6) *Edge.*—Serrated.

(7) *Serration.*—Serrulate.

(8) *Leaf stem.*—Color — lt green 137B, turning green 138B.

(9) *Stipules.*—Slightly bearded, 1 cm.

(10) *Rachis.*—Medium — upper side not groved.

(11) *Resistance: Blackspot — Average. To disease.*—Mildew — Average. Rust — Average.

D. Wood:

(1) *New wood.*—Color — Light green near 137B. Bark — smooth.

(2) *Old wood.*—Color — near 138B. Bark — smooth, with sturdy growth with 1 cm internodes.

E. Thorns:

(1) *Thorns.*—Quantity (main stalk) — heavy. On laterals from stalk — plentiful. Form — needle, declining. Length — $\frac{1}{3}$ cm. Color — cream turning to light brown. Position — ordinary.

(2) *Prickles.*—Profuse.

F. Winter hardiness: Requires ordinary protection in extreme climates.

I claim:

1. A new miniature rose variety having variegated red and white flower coloring.

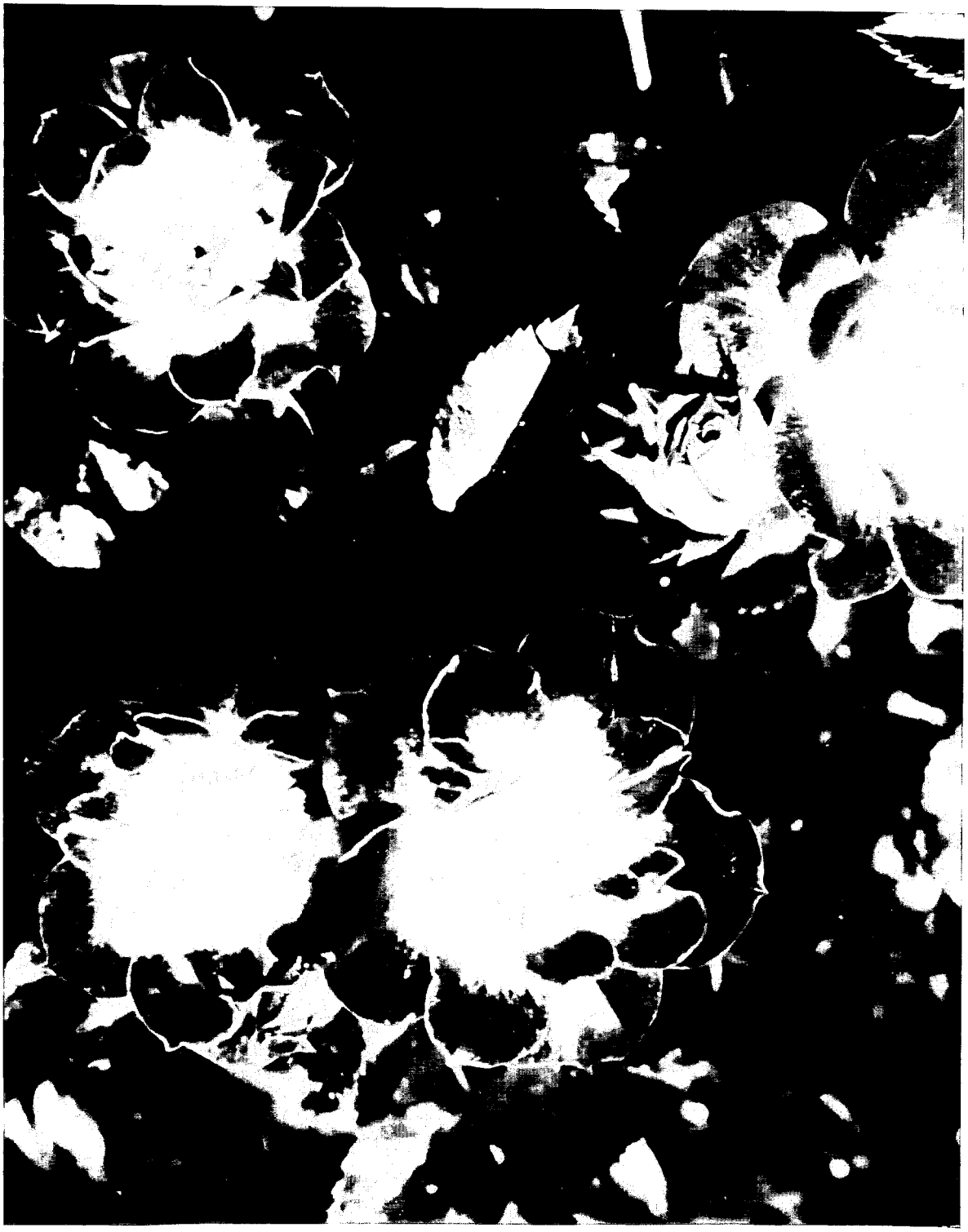

* * * * *